(12) United States Patent
Saba

(10) Patent No.: US 6,505,937 B1
(45) Date of Patent: Jan. 14, 2003

(54) TEST SLIDE FOR A VISION TESTING APPARATUS

(75) Inventor: Adeeb G. Saba, Midlothian, VA (US)

(73) Assignee: Titmus Optical, Inc., Petersburg, VA (US)

(*) Notice: Subject to any disclaimer, the term of this patent is extended or adjusted under 35 U.S.C. 154(b) by 0 days.

(21) Appl. No.: 09/539,779

(22) Filed: Mar. 31, 2000

(51) Int. Cl.[7] .................................................. A61B 3/02
(52) U.S. Cl. ....................................... 351/239; 351/243
(58) Field of Search .................................. 351/237, 238, 351/239, 240, 241, 242, 243, 222

(56) References Cited

U.S. PATENT DOCUMENTS 4,550,990 A * 11/1985 Trispel et al. ................ 351/243

* cited by examiner

Primary Examiner—George Manuel
(74) Attorney, Agent, or Firm—John H. Thomas, P.C.

(57) ABSTRACT

A test slide is designed for use in a vision testing apparatus. The test slide comprises several component layers. Those layers include a light diffusing layer, an optotype film layer, a color correcting film layer, a frame separator, and a clear glass layer wherein the components are laminated together in the order identified.

7 Claims, 2 Drawing Sheets

TEST SLIDE FOR A VISION TESTING APPARATUS

This invention is directed to test slides for use in a vision testing apparatus. Specifically, a test slide includes component layers designed to reduce the occurrence of interference fringes that can disrupt the effectiveness of the vision testing apparatus.

BACKGROUND OF THE INVENTION

Vision testing equipment commonly includes test slides that display the visual optotypes that are designed to evaluate various vision abilities. The test slides may be permanently fixed in an apparatus. Alternatively, the test slides may be removably mounted in the apparatus to allow for various types of tests to be performed by varying the size, orientation, shape, color, etc. of the optotype being displayed. This removable mounting technique allows for custom selection of slides in a given testing apparatus. It also allows for the replacement of slides if they become faded, distorted, or otherwise no longer effectively operable.

There are many types of test slides currently in use. Some slides are made up of a monolayer of film generally similar to projection slide systems. Some slides have optotypes directly printed onto a single glass layer. Most slides, however, are multiple layer, laminated assemblies. These layers may include a light diffusing layer, a color correction layer, an optotype layer, a clear glass cover layer, or other types of layers. These layers in various combinations may be used by different slide makers for different applications.

A potential problem that arises when laminating transparent layers together, particularly relatively thin layers as is common in test slides, is the appearance of interference fringes (also called Newton rings) when looking at the slide. Simply described, interference fringes are the "rainbows" that are visible on the slide that are the result of imperfect flatness (or imperfect lamination) of adjacent thin transparent layers, particularly a thin film next to flat glass plate. The light and dark rings are produced by the interference of light at the film of air between the surfaces. The rainbows that result from this physical phenomena can be distractive and, possibly, disruptive of the vision test that is being performed. Even if the slides do not have a significant rainbow effect when new, rainbows can develop and get worse over time after the slide is in the apparatus.

Historically, in order to address the issue of interference fringes or rainbows, slide manufacturers have required very tight specifications regarding the flatness of the various layers that comprise the slide. These strict specifications mean that the components are typically relatively expensive. Alternatively, the layers have been separated into different slides, but this solution is limited by the space that is available in the apparatus itself. Another attempted solution is coating of glass to achieve, for instance, color correction in order to reduce the number of layers. This solution, however, has many of the foregoing drawbacks with respect to flatness.

SUMMARY OF THE INVENTION

Accordingly, it is an objection of the present invention to overcome the foregoing drawbacks and provide a test slide having reduced or no interference fringes. Upon further study of the specification and appended claims, further objects and advantages of this invention will become apparent to those skilled in the art.

In one embodiment, the invention includes a test slide for use in a vision testing apparatus comprising several component layers. The layers include a light diffusing layer, an optotype film layer, a colored film layer, a frame separator and a clear glass layer. The components are laminated together in the order identified. The laminated slide may further comprise an opaque tape for securing the edges of the components together to form the laminate slide.

In a further embodiment, a test slide is used in a vision testing apparatus, the slide comprising several component layers. Those component layers include a clear glass layer, a frame separator laminated adjacent to the clear glass layer, and an optotype film layer.

In a still further embodiment, a test slide is designed for use in a vision testing apparatus wherein the apparatus comprises a light source and a viewer. The test slide is mounted between the light source and the viewer, and the test slide has a first side facing the light source and a second side facing the viewer. The test slide comprises an optotype film layer and a colored film layer wherein the colored film layer is on the side of the optotype film layer facing the viewer.

Another embodiment includes a test slide for use in a vision testing apparatus. The test slide is comprised of a lamination of a plurality of layers wherein a frame separator is one of the layers.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
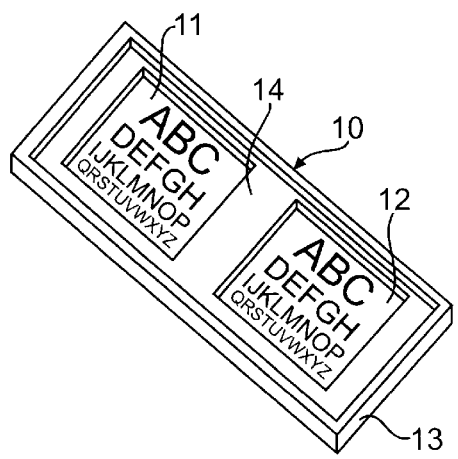
FIG. 1 is a perspective view of a test slide in accordance with the present invention.

In a preferred embodiment, a test slide is a five layer laminate. FIG. 1 displays a fully-assembled test slide 10 that is rectangular in shape and adapted to fit into a vision tester such as that described in U.S. Pat. No. 4,740,072, the disclosure of which is incorporated herein by reference. The relative placement of a test slide within an assembly is discussed in the '072 patent, and that knowledge is assumed herein. The back side 15 of the slide (see FIG. 3) faces the light source in a vision testing apparatus while the front side 14 of the slide 10 displayed in FIG. 1 faces a viewing device or viewer portion of a testing apparatus. As shown in FIG. 1, there is a right pattern 12 and a left pattern 11 of the test slide 10. These patterns 11 and 12, referred to generically as optotypes, are constructed to provide very precise test patterns to the test subject. Many different optotypes may be used on the test slides to test for a wide range of visual abilities.

The laminate structure for a slide is cost effective for many reasons. Primarily, the laminate structure allows for individual component layers to be varied depending on specifications of a particular vision testing apparatus and the different visual test parameters that can be performed on that apparatus.

Figure 2:
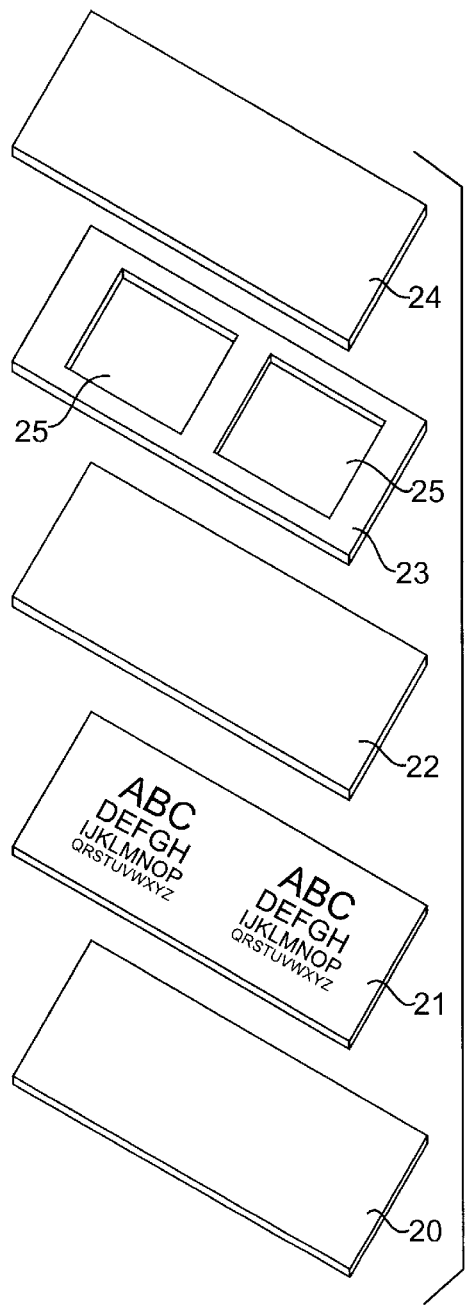
FIG. 2 is an exploded view of the test slide shown in FIG. 1.
Figure 3:
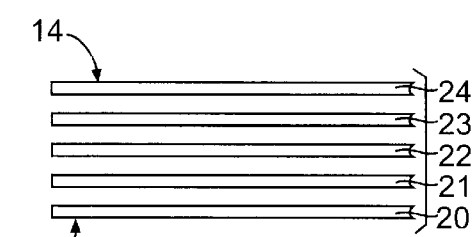
FIG. 3 is a side elevation, exploded view of the test slide shown in FIGS. 1 and 2.

Turning now to FIGS. 2 and 3, a light diffuser 20 is the outside layer on the back side 15 of the test slide shown in FIG. 1. In a preferred embodiment, the light diffuser 20 is made of glass rather than a plastic film so that it is less easily scratched. Nevertheless, the light diffuser 20 can be made of any plastic or glass material. The light diffuser 20 is preferably made of frosted or opal glass which acts to diffuse the light entering through the glass from illumination bulbs that are the light source in a conventional vision testing apparatus. The opal glass diffusion layer 20 is designed to enhance the clear and crisp images of the test pattern optotypes visible to a test subject. The purpose of the diffusion layer 20 is to diffuse uniformly a concentrated source of light. As a result of the light diffuser 20, the light rays striking the eye of the test subject are parallel and are normal to the plane of the opal glass diffuser layer 20. If the opal glass layer 20 was not provided, the light rays striking the eye of the test subject would not be parallel since they all originate from a single point (the illumination bulb light source).

Adjacent to the light diffuser layer 20 is the optotype film layer 21. Again, this layer 21 is preferably made of a plastic film, because a negative can be made at low cost with different optotype test patterns. The film 21 is typically coated with an emulsion that is conventional in the photography art. Alternatively, however, this film layer 21 could be glass. In the preferred embodiment, the optotype film 21 is made of polyester, because polyester is stiff and durable in the conditions within the apparatus and is very printable. Other films (coated or uncoated) such as vinyls, polyolefins, and polystyrenes, including coextruded films, could also be used as the optotype film. As shown, the test pattern or optotype is shown in two different locations, i.e., the right pattern 12 and left pattern 11 to test the vision of the two eyes of a test subject.

The next adjacent film layer in this embodiment is the colored film layer 22. As known in the industry for many years, a blue film can be used to "correct" the tint and to make incandescent light more like natural light. In the preferred embodiment, where the light source is a conventional, incandescent bulb, the film 22 is generically blue and is termed a "tungsten conversion filter." A whole range of suitable film products that are acceptable for given applications are available from Rosco Laboratories, Inc., Stanford, Conn. Other colored film layers may be substituted or also included for the purposes of other specific tests, for instance, a yellow film alone may be inserted to create a colored background for testing depth perception.

The next layer is the frame separator 23. This separator 23 has an outer edge, in this case, a rectangular outer edge, so that it can be aligned with the other layers in the slide assembly. This layer can be very thin, with the minimum thickness being at least several times the greatest wavelength of colors in the visible spectrum. Preferably, the film separator 23 is black vinyl and has a thickness between 0.006 inches and 0.010 inches. Importantly, however, it is much thicker than the wavelengths of the various colors of the visible spectrum so that by separating the film layer 22 from the clear glass layer 24, the occurrence of rainbows or interference fringes is minimized or eliminated. The apertures or windows 25 in the middle of the frame separator 23 are designed to frame the optotypes that are contained on the various test patterns. Preferably, this frame separator 23 is opaque to reduce the possibility of incidental light reflecting into the slide from the edges. Also, the frame separator 23 is preferably black and of a matte finish so that there is reduced reflection of incidental light as well as no potential for interference fringes on the portion of the frame separator that is laminated against the colored film 22 and against the clear glass layer 24.

The final layer is a flat, clear glass layer 24. This layer 24 is preferably glass in order to prevent the potential for scratching on the slide. Also, because it is glass, it is easily cleaned and more durable in the conditions of the vision tester. Like the opal glass layer 20, this clear glass layer 24 may alternatively be made of plastic as well as the glass in the preferred embodiment.

The edge tape 13 shown in FIG. 1 holds together the layers of the laminated slide. The tape 13 is preferably made of opaque material to prevent incidental light from seeping in between the laminated layers. In the preferred embodiment, the tape 13 is a black tape.

Figure 4:
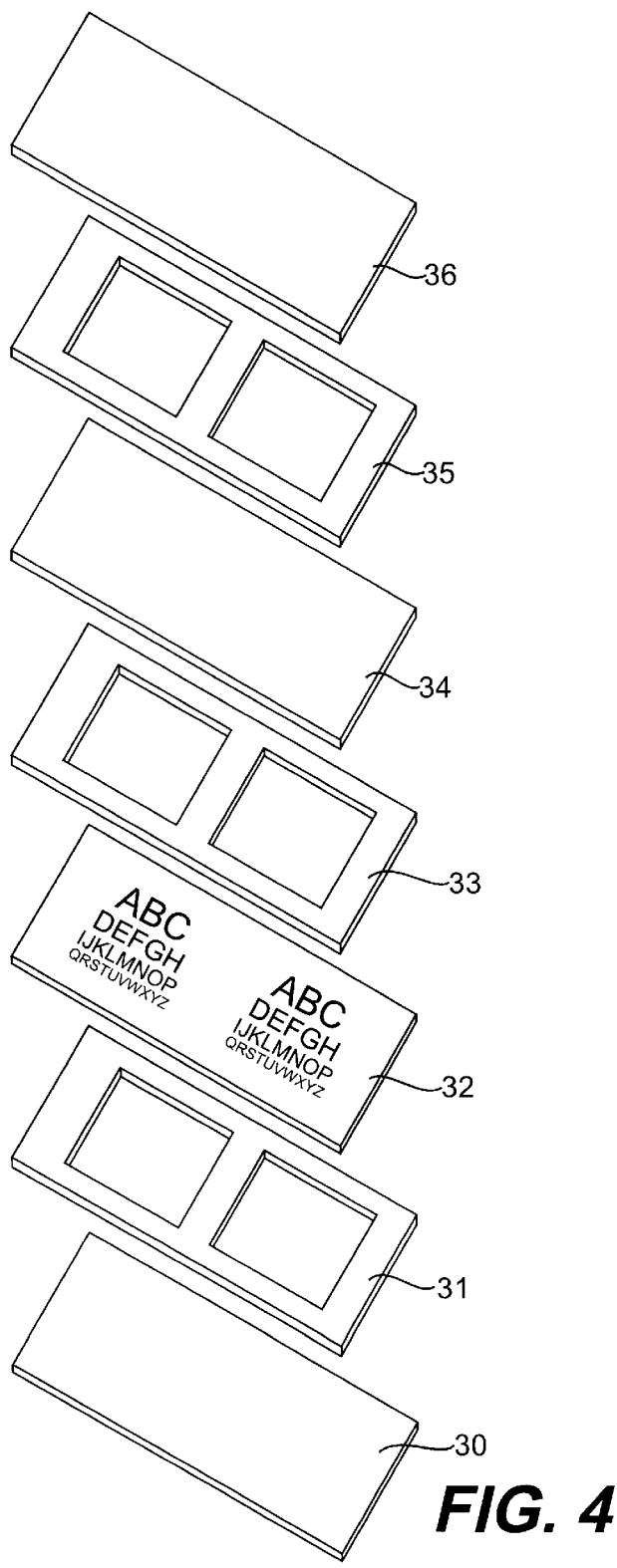
FIG. 4 is an exploded view of an alternative embodiment of the test slide in accordance with the present invention.
Figure 5:
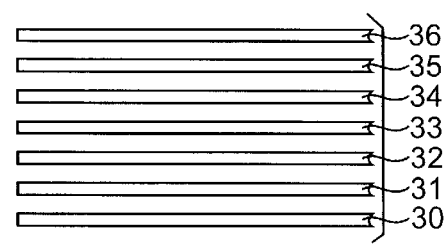
FIG. 5 is a side elevation, exploded view of the slide shown in FIG. 4.

FIGS. 4 and 5 display an alternative embodiment of a test slide. The test slide is similar to the test slide shown in FIGS. 1–3 in that the light diffusing layer 30, the optotype film layer 32, the colored film layer 34, and the clear glass layer 36 are all arranged in that order in the laminate slide. Instead of a single frame separator, however, there is a frame separator 31, 33, 35 between each of the layers so that there are in fact three frame separators in the laminate slide assembly shown in FIG. 4 and FIG. 5.

The order of the layers in a test slide is significant. The light diffusing layer or opal glass layer is preferably the outside layer on the side of the slide that will be facing the light source in the vision testing apparatus. This opal glass is preferably adjacent the optotype layer so that the diffused light from the opal glass layer is immediately shown through the optotype film layer. This creates a more clear and crisp figure. It is possible to insert a frame separator between the light diffusing layer and the optotype layer (FIGS. 4 and 5) to eliminate any possibility of interference fringes or rainbows between those two flat layers, but this could possibly raise the issue of shadows occurring within the slide. It is preferable, therefore, to place the optotype film directly adjacent the opal glass layer. Also, as noted earlier, if the light source is diffused by other means, for instance a separate slide, the opal glass layer may not be necessary and a separate clear glass layer may be used or no additional layer at all may be necessary.

Relatively speaking, it is also important that the colored film layer be placed on the top side of the optotype, i.e., the side of the optotype film away from the light source and facing the viewer in the vision testing assembly. By placing the color layer on this top side of the optotype film, the interference fringes and rainbows are reduced. Again, a frame separator could be inserted between the optotype film and the colored film to further reduce or eliminate the potential for interference fringes in the slide. Also, to the extent the light from the light source has been "corrected" or otherwise tinted in a vision tester before reaching the slide, then the colored film layer may not be necessary at all.

The frame separator is important to place between the colored film and the clear glass top layer. The lamination of the colored film to the clear glass layer is prone to the formation of interference fringes. Therefore, by using the separator, an air gap is formed between the layers that effectively prevents the formation of rainbows. As noted earlier, a frame separator can be used between any two or between all of the layers of the test slide laminate. Obviously, the separator is not effective in reducing interference fringes when it is the outside layer of the test slide assembly. Also, one of the problems with inserting too many separator layers in a test slide is the potential that internal shadows may form and internally reflected light may find its way into the test slide to reduce the clarity and crispness of the test optotypes. In a vision testing assembly that is sealed from outside light, however, incidental reflected light is not likely to be a problem. For instance, in the vision tester described in the '072 patent, there is no outside light allowed into the assembly to dull or otherwise interfere with the light source and the image that is visible to the test subject. Finally, the use of too many separator layers may also result in a slide that is too thick to be interchangeable in some assemblies. Therefore, separators may not be possible for use in all slide applications. By using separators, less stringent specifications may be available to a slide maker with respect to the flatness of the glass layers and the film layers that make up the slide laminate.

Further, although the test slide assembly described in these preferred embodiments includes a specific order of film layers within a slide assembly, it is obvious to those of skill in the art that the use of a frame separator may be used when the order of layers is varied or different. In fact, not all of the layers need to be present in a test slide. For instance, the color correction film or the light diffusing layer may both be layers that are otherwise accounted for within a vision testing assembly. In those cases, fewer layers are required to be used in the test slide laminate.

While the invention has been described in connection with what is presently considered to be the most practical and preferred embodiments, it is to be understood that the invention is not limited to the disclosed embodiment but, on the contrary, is intended to cover various modifications and equivalent arrangements included within the spirit and the scope of the appended claims, which scope is to be accorded the broadest interpretation so as to encompass all such modifications and equivalent structures.

What is claimed is:

1. A test slide for use in a vision testing apparatus comprising the following component layers:
   a) a light diffusing layer,
   b) an optotype film layer,
   c) a colored film layer,
   d) a frame separator, and
   e) a clear glass layer
   wherein the component layers are laminated together in the order identified.

2. The test slide described in claim 1, wherein the outside edge dimensions of each component are substantially the same.

3. The test slide described in claim 2, further comprising opaque tape for securing the edges of the components together to form the laminate slide.

4. The test slide described in claim 1, wherein the frame separator is comprised of a matte black material.

5. A test slide for use in a vision testing apparatus wherein the apparatus comprises a light source and a viewer and the test slide is mounted between the light source and the viewer, and further wherein a first side of the test slide faces the light source and a second side of the test slide faces the viewer, the test slide comprising:
   a) a optotype film layer, and
   b) a colored film layer, wherein the colored film layer is on the side of the optotype film layer facing the viewer.

6. The test slide described in claim 5 further comprising a light diffusing layer wherein the light diffusing film layer is on the side of the optotype film layer facing the light source.

7. A test slide for use in a vision testing apparatus comprising the following component layers:
   a) a light diffusing layer,
   b) a first frame separator,
   c) an optotype film layer,
   d) a second frame separator,
   e) a colored film layer,
   f) a third frame separator, and
   g) a clear glass layer
   wherein the component layers are laminated together in the order identified.

* * * * *